United States Patent [19]

Lattrell et al.

[11] Patent Number: 5,036,063
[45] Date of Patent: Jul. 30, 1991

[54] PENEM DERIVATIVES

[75] Inventors: Rudolf Lattrell, Königstein/Taunus; Walter Dürckheimer, Hattersheim am Main; Gerhard Seibert, Darmstadt, all of Fed. Rep. of Germany

[73] Assignee: Hoechst Aktiengesellschaft, Frankfurt am Main, Fed. Rep. of Germany

[21] Appl. No.: 440,797

[22] Filed: Nov. 24, 1989

[30] Foreign Application Priority Data

Nov. 26, 1988 [DE] Fed. Rep. of Germany ....... 3839987

[51] Int. Cl.$^5$ .................... C07D 499/00; A61K 31/43
[52] U.S. Cl. .................... 514/192; 540/310; 514/195
[58] Field of Search ............... 540/222, 310; 514/195, 514/192

[56] References Cited

U.S. PATENT DOCUMENTS 4,386,030  5/1983  Christensen et al. ....... 260/245.2 R

FOREIGN PATENT DOCUMENTS

11482/88  8/1988  Australia .
0002210  6/1979  European Pat. Off. .
0278911  8/1988  European Pat. Off. .

Primary Examiner—Nicholas S. Rizzo
Attorney, Agent, or Firm—Finnegan, Henderson, Farabow, Garrett, and Dunner

[57] ABSTRACT

Penem derivatives of the formula

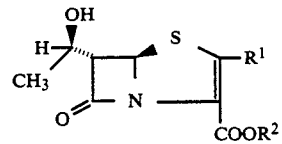

having $R^1$ equal to 3-oxocyclobutyl and $R^2$ equal to H or an ester-forming group, pharmaceutical preparations active against bacterial infections and which contain penem derivatives of this type, processes for the preparation of the penem derivatives and the pharmaceutical preparations, and use of the penem derivatives for the control of bacterial infections are described.

5 Claims, No Drawings

PENEM DERIVATIVES

DESCRIPTION

The invention relates to penem derivatives which are substituted in the 2-position of the penem ring by a cycloaliphatic radical and which possess a very good antimicrobial action against gram-positive and gram-negative bacteria and are therefore suitable as pharmaceuticals for the treatment of microbial infections, and to processes for their preparation.

Penem derivatives and their antibacterial activity are known, for example from the Patent Nos. U.S. Pat. Nos. 4,386,030, EP 2,210 or EP 278,911. However, these substances are still not satisfactory in any respect.

The invention therefore relates to penem derivatives of the formula I

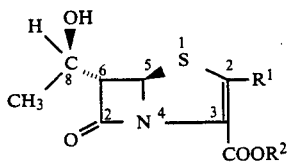

and their pharmaceutically tolerable salts, in which

R$^1$ denotes
  C$_3$-C$_6$-oxocycloalkyl
  C$_3$-C$_6$-(1,1-bis-C$_1$-C$_3$-alkoxy) cycloalkyl
  C$_3$-C$_6$-(1,1-C$_2$-C$_3$-alkylenedioxy) cycloalkyl
  C$_3$-C$_6$-(C$_1$-C$_3$-alkylimino) cycloalkyl
  C$_3$-C$_6$-aryliminocycloalkyl (where aryl is equal to phenyl, thienyl or furyl)
  C$_3$-C$_6$-hydroxyiminocycloalkyl
  C$_3$-C$_6$-(C$_1$-C$_3$-alkyloxyimino) cycloalkyl
  in which the cycloalkyl radical is unsubstituted, or monosubstituted or disubstituted by C$_1$-C$_3$-alkyl, preferably methyl, C$_1$-C$_3$-alkoxy, preferably methoxy, by halogen, preferably chlorine, or by methylene, R$^2$ denotes hydrogen
  C$_1$-C$_5$-alkanoyloxy-C$_1$-C$_3$-alkyl,
  C$_1$-C$_5$-alkoxycarbonyloxy-C$_1$-C$_3$-alkyl,
  5-methyl-1,3-dioxolen-2-on-4-yl-methyl phthalidyl
and in which the preferred stereochemistry in position 5 is R, in position 6 is S and in position 8 is R.

Possible particularly preferred groups are, for example, the following groups:

R$^1$ 3-oxocyclobutyl, functional derivatives of the keto group, such as acetals

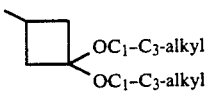

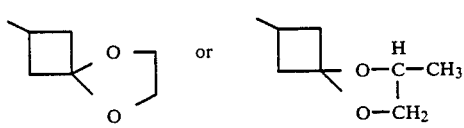

Schiff bases

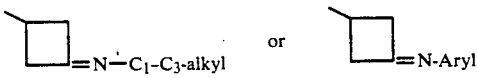

oximes

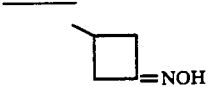 or 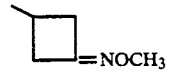

in which n=0–3, and aryl denotes phenyl, thienyl or furyl,

R$^2$ hydrogen ester radicals, which can be eliminated in vivo with the formation of the free carboxylic acid, for example acetoxymethyl, propionyloxymethyl, isopropionyloxymethyl, N-butyryloxymethyl, isobutyryloxymethyl, pivaloyloxymethyl, isovaleryloxymethyl, 1-acetoxyethyl, 1-acetoxypropyl, 1-pivaloyloxyethyl, 1-methoxycarbonyloxyethyl, 1-ethoxycarbonyloxyethyl, 1-isopropoxycarbonyloxyethyl, methoxycarbonyloxymethyl; phthalidyl,5-methyl-1,3-dioxolen-2-on-4-ylmethyl.

The invention furthermore includes processes for the preparation of compounds of the formula I and their pharmaceutically tolerable salts which comprise
(a) reacting a compound of the formula II

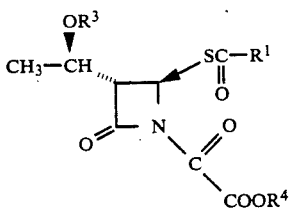

in which R$^1$ has the meaning mentioned for formula I,
R$^3$ denotes hydrogen or a hydroxyl protecting group,
R$^4$ denotes a carboxyl protecting group, with trialkyl phosphites,
(α) removing an optionally present protecting group R$^3$ and R$^4$ and
β) if necessary, converting the product obtained into a pharmaceutically tolerable salt,
or
(b) cyclizing a compound of the formula III

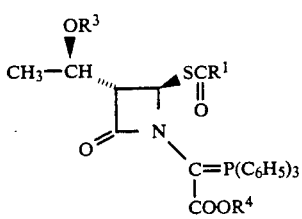

in which R$^1$, R$^3$ and R$^4$ have the meaning mentioned for formula II, by heating,
α) removing an optionally present protecting group and
β) if necessary, converting the product obtained into a pharmaceutically tolerable salt and
(c) if it is intended to prepare functional derivatives of keto compounds, converting the compounds of the formula I obtained by process variant a) or b) and having a keto group in the radical R$^2$ into, for example, acetals, Schiff bases or oximes in a manner known per se, and (d) if it is intended to obtain esters which can be cleaved in vivo, converting the compounds of the formula I obtained by process variants a), b) or c) and in which $R^2$ stands for hydrogen into the esters mentioned under $R^2$ in a manner known per se.

According to process a), the compounds of the formula II are cyclized by the action of 2-4 equivalents of trialkyl phosphite, preferably trimethyl phosphite or triethyl phosphite. The reaction is carried out at temperatures between 60° C. and 200° C., preferably between 90° C. and 150° C. in an inert aprotic solvent. Suitable solvents are, for example, chlorinated hydrocarbons such as 1,1,2-trichloroethane, and aromatic hydrocarbons such as benzene, toluene or xylene. The reaction time depends on the reactants, the temperature and the solvent and is normally between ½ and about 72 hours. According to this process, the compounds of the formula I are initially obtained in protected form.

The protecting groups are removed in a manner known per se. Preferred protecting groups $R^3$ for the 8-hydroxyl group are, for example, the trimethylsilyl, the tetrahydropyranyl or 2-methoxyprop-2-yl group, which is removed by acid hydrolysis or the tert-butyldimethylsilyl group, which is removed by means of tetrabutylammonium fluoride.

Suitable protecting groups $R^4$ for the carboxyl group are in particular the hydrogenolytically removable p-nitrobenzyl group, the allyl or 2-chloroallyl group, which is removed using $Pd[P(C_6H_5)_3]_4$ or the trimethylsilylethyl group, which is removed by means of $Bu_4NF$.

The starting compounds of the formula II are obtained by processes which are known from the literature.

According to process b), a compound of the formula III is cyclized with the formation of a protected compound of the formula I. The reaction preferably proceeds in an inert aprotic solvent such as toluene, xylene, dioxane, tetrahydrofuran or diethoxyethane at temperatures between room temperature and the reflux temperature of the reaction mixture. After the cyclization reaction, the reaction products are as usual purified by column chromatography or crystallization. The protecting groups are then removed as described above. The starting compounds of the formula III are likewise obtained by processes which are known from the literature.

It it is intended to obtain compounds of the formula I, in which $R^2$ stands for $C_1$–$C_5$-alkanoyloxy-$C_1$–$C_3$-alkyl, $C_1$–$C_5$-alkoxycarbonyloxy-$C_1$–$C_3$-alkyl, phthalidyl or 5-methyl-1,3-dioxolene-2-on-4-ylmethyl, according to process d), the compounds of the formula I, in which $R^2$ denotes hydrogen, are reacted in a known way with a compound of the general formula IV

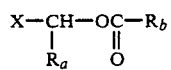
                          IV in which $R_a$ denotes hydrogen or a $C_1$–$C_2$-alkyl group, $R_b$ denotes a $C_1$–$C_5$-alkyl or a $C_1$–$C_5$alkoxy group, or with V, or VI

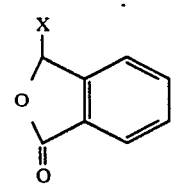

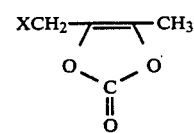

in which X stands for halogen, preferably chlorine, bromine or iodine.

Processes are used which are known for esterification reactions.

Pharmaceutially tolerable salts of the compounds of the formula I which may be mentioned are, for example, lithium, sodium, potassium, calcium or magnesium salts or salts with organic amines such as diethylamine, benethamine, piperazine or tromethamine.

The compounds of the formula I obtained according to the invention and their pharmaceutically tolerable salts show remarkably good antibacterial activity both against gram-positive and gram-negative bacterial microorganisms.

The compounds of the formula I are also unexpectedly highly effective against penicillinase-forming and cephalosporinase-forming bacteria. Since they additionally show favorable toxicological and pharmacological properties, they are useful chemotherapeutics.

The invention therefore also relates to pharmaceutical preparations for the treatment of microbial infections, which contain one or more of the compounds according to the invention.

The products according to the invention can also be used in combination with other active compounds, for example from the penicillin, cephalosporin or aminoglycoside series.

The compounds of the formula I and their pharmaceutically tolerable salts can be administered orally, intramuscularly or intravenously.

Pharmaceutical preparations which contain one or more compounds of the formula I as active compound can be produced by mixing the compounds of the formula I with a number of pharmacologically tolerable excipients or diluents, such as fillers, emulsifiers, lubricants, flavor enhancers, colorants or buffer substances and brought into a suitable galenical preparation form, such as tablets, coated tablets, capsules or a suitable suspension or solution for parenteral administration.

Suitable excipients or diluents which may be mentioned are, for example, tragacanth, lactose, talc, agar agar, polyglycols, ethanol and water. Buffer substances are, for example, organic compounds, such as, for example, N,N'-dibenzylethylenediamine, diethanolamine, ethylenediamine, N-methylglucamine, N-benzylphenethylamine, diethylamine, tris-(hydroxymethyl)aminomethane (tromethamine), or inorganic compounds such as phosphate buffer, sodium bicarbonate or sodium carbonate. Suspensions or solutions in water with or without buffer substances are preferably suitable for parenteral administration. It is also possible to administer the active compound as such without excipients or diluents in a suitable form, for example in capsules.

Suitable doses of the compounds of the formula I or their pharmaceutically tolerable salts are about 0.4 g, preferably 0.5 g per day up to a maximum of about 20 g, preferably 4 g/day for an adult of about 75 kg body weight.

Individual or, in general, multiple doses may be administered, it being possible for the individual dose to contain the active compound in an amount of about 50 to 1000 mg, preferably of about 100 to 500 mg.

The following exemplary embodiments of 5R, 6S-compounds which can be prepared according to the invention serve to illustrate the invention further.

EXAMPLE 1

(5R, 6S)-6-[(1R)-Hydroxyethyl]-2-(3-oxocyclobutyl)-penem-3-carboxylic acid

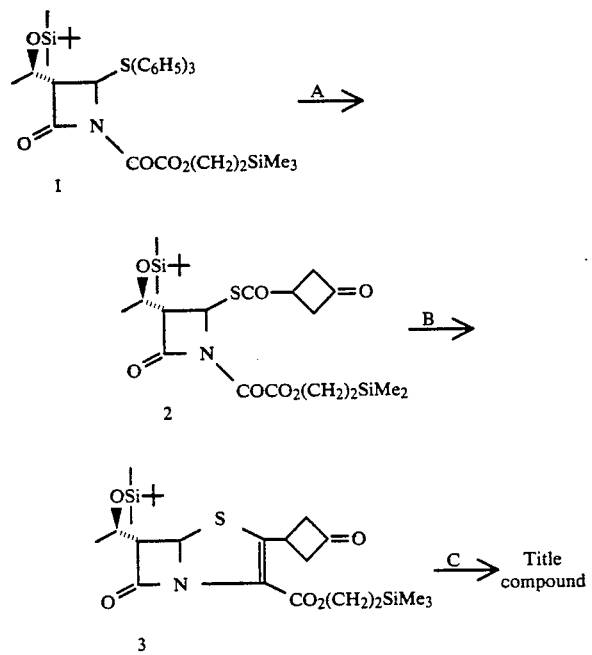

Step A:

A solution of 562 mg (3.3 mmol) of silver nitrate, 260 mg (3.3 mmol) of pyridine and 100 mg (3.12 mmol) of methanol in 6 ml of acetonitrile is added at 0° C. under argon during the course of 5 minutes to a solution of 2.04 g (3 mmol) of 1 in 12 ml of acetonitrile. The mixture is stirred for one hour in an ice bath, the acetonitrile is distilled off in vacuo and the residue is dissolved in 40 ml of methylene chloride. The solution is washed twice with 15 ml each of water, dried over magnesium sulfate, filtered and concentrated to a volume of 20 ml. A solution of 510 mg (3.8 mmol) of 3-oxocyclobutanecarbonyl chloride in 5 ml of methylene chloride is added at 0° C. to this solution of the silver salt. The mixture is stirred for 2 hours in the ice bath and for 30 minutes at room temperature, and the precipitated silver chloride is filtered off with suction and washed with methylene chloride. The organic phase is washed twice with 15 ml each of water and dried. After distilling off the solvent, the residue is chromatographed on silica gel, which has been deactivated using 10% of water, using cyclohexane:ethyl acetate (5:1). 1.05 g of 2 (66%) is obtained as a colorless viscous oil.

$^1$H-NMR (CDCl$_3$):δ=0.06 (s, 9H), 0.09 (s, 6H), 0.86 (s, 9H), 1.12 (m, 2H, CH$_2$Si), 1.26 (d, J-6 Hz, 3H, CHC$_3$), 3.2–3.6 (m, 5 cyclobutane-H), 3.49 (dd, 3-H), 4.38 (m, 3H, CO$_2$CH$_2$ and CH—CH$_3$), 6.01 (d, J=2.5 Hz, 4-H).

Step B:

A solution of 530 mg (1 mmol) of 2 in 25 ml of dry toluene is heated to boiling and a solution of 644 mg (4 mmol) of triethyl phosphite in 2.5 ml of toluene is then added. The mixture is heated under reflux for a further 5 hours, cooled and washed with 5 ml of 1N KHSO$_4$, then five times with 25 ml each of water. After drying (MgSO$_4$), the solvent is removed in vacuo and the residue is chromatographed on silica gel, deactivated with 10% of water, using toluene/ethyl acetate (10:1). After evaporating the product fractions, 375 mg (75%) of 3 are obtained as a colorless crystalline solid.

$^1$H-NMR (CdCl$_3$) δ=0.06 (s, 9H), 0.10 (s, 6H), 0.88 (s, 9H), 1.08 (m, 2H, CH$_2$Si), 1.28 (d, J=6 Hz, 3H, CHCH$_3$), 3.15–3.55 (m, 5 cyclobutane-H), 3.70 (dd, J=5 and 1 Hz, 6-H), 4.25 (m, 3H, CO$_2$CH$_2$ and CHCH$_3$), 4.52 (m, 1 cyclobutane-H), 5.58 (d, J=1 Hz, 5-H).

Step C: Preparation of the title compound 3 ml (3 mmol) of a 1N Bu$_4$NF solution in tetrahydrofuran are added to a solution of 318 mg (0.6 mmol) of 3 in 1.2 ml of tetrahydrofuran. After 10 minutes at room temperature, 12 ml (3.6 mmol) of 0.3N acetic acid are added and the solution is concentrated to 10 ml in vacuo. The aqueous solution is chromatographed on adsorber resin XAD-2 (2×25 cm column). Eluent: water, followed by water:isopropanol (9:1). The product fractions are freeze-dried and the tetrabutylammonium salt of the title compound obtained (120 mg) is rechromatographed on reverse phase silica gel RP 18 using water:isopropanol (9:1). After freeze-drying the product fractions, 39 mg (23%) of an amorphous colorless solid are obtained.

$^1$H-NMR (DMSO-d6)$_3$ δ=1.16 (d, J=6 Hz, CHCH$_3$), 2.94–3.18 (m, 2 cyclobutane-H), 3.20–3.45 (m, 2 cyclobutane-H), 3.56 (dd, J=5 and 1 Hz, 6-H), 3.93 (m, CHCH$_3$), 4.72 (m, 1 cyclobutane-H), 5.62 (bs, OH), 5.50 (d, J=1 Hz, 5-H).

EXAMPLE 2

(5R, 6S)-6-[(1R)-Hydroxyethyl]-2-(3,oxycyclobutyl)-penem-3-carboxylic acid potassium salt

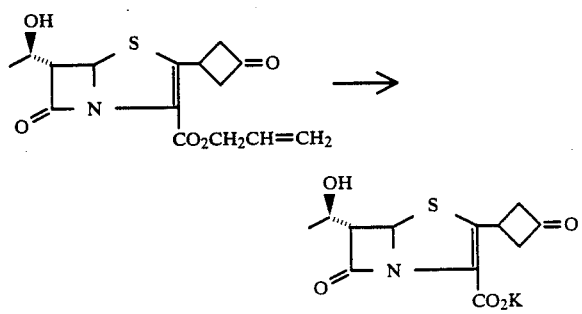

A solution of 4.57 g (25 mmol) of 2-ethylenehexanoric acid potassium salt in 50 ml of ethyl acetate and then 1.97 g (7.5 mmol) of triphenylphosphine and 1.27 g (1.1 mmol) of tetrakis-(triphenylphosphine)palladium(0) are added at room temperature under argon to a solution of 8.1 g (25 mmol) of 1—this starting compound of m.p. 121°-123° C. was prepared from the compound 1 of example 3 in analogy to the reaction sequence A→B→C indicated there using 3-oxocyclobutanecarbonyl chloride—in 80 ml of methylene chloride and 30 ml of ethyl acetate. The mixture is stirred at room temperature for 4 hours, diluted using 300 ml of methylene chloride and extracted twice using 250 ml of water each time. The aqueous phase is washed three times using 100 ml of methylene chloride each time and freeze-dried. 7.5 g of brown amorphous product remain. The latter is dissolved in 20 ml of water and diluted using 100 ml of acetone. Crystallazation of the potassime salt occurs after triturating briefly. After 4 hours cooling in the ice bath, the precipitate is filtered off with suction, washed with acetone and dried over $P_2O_5$. Yield: 4.7 g. A further 0.7 g is isolated from the concentrated mother liquor.

Total yield: 5.4 g (67.3% of theory).

$^1$H-NMR (DMSO-$d_6$): $\delta$=1.16 (d, J=6 Hz, 3H, CHCH$_3$), 2.90-3.38 (m, 4 cyclobutane-H), 3.45 (dd, J=5 and 1 Hz, 6-H), 3.90 (m, 1H, CHCH$_3$), 4.88 (m, 1 cyclobutane-H), 5.21 (d, J=4 Hz, OH), 5.45 (d, J=1 Hz, 5-H).

EXAMPLE 3

5R, 6S-6-[(1R)-Hydroxyethyl]-2-(3,3-dimethoxycyclobutyl)-penem-3-carboxylic acid sodium salt

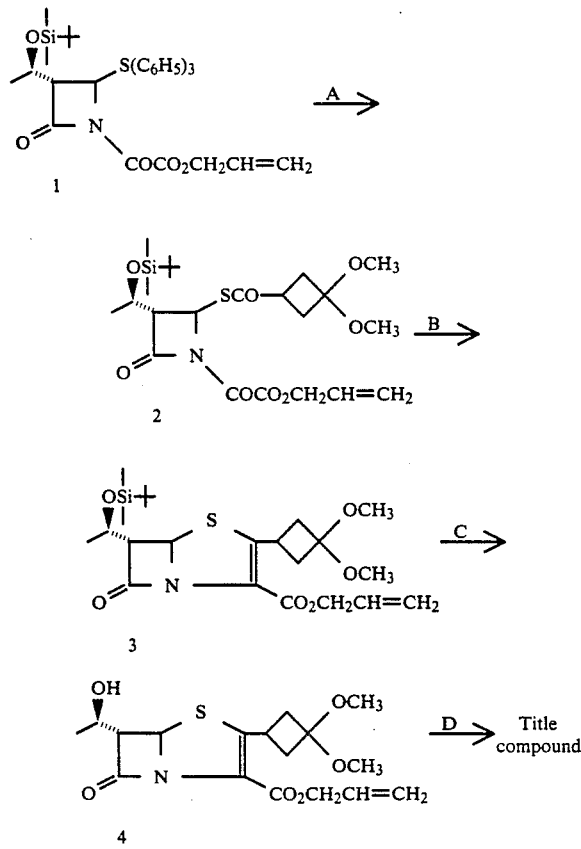

Step A:

A solution of 562 mg (3.3 mmol) of silver nitrate, 260 mg (3.3 mmol) of pyridine and 100 mg (3.12 mmol) of methanol in 6 ml of acetonitrile are added at 0° C. under argon during the course of 5 minutes to a solution of 1.85 g (3 mmol) of 1 in 12 ml of acetonitrile. The mixture is stirred in an ice bath for one hour, the solvent is distilled off in vacuo and the residue is dissolved in 40 ml of methylene chloride. The solution is washed twice with 15 ml each of water, dried over MgSO$_4$ and concentrated to 20 ml. A solution of 4 mmol of crude 3,3-dimethoxycyclobutanecarbonyl chloride—prepared from 4 mmol of sodium salt and 4 mmol of oxalyl chloride in 5 ml of methylene chloride for 30 minutes at 5° C. to room temperature—is added at 0° C. to a solution of the silver salt in methylene chloride. After stirring for 2 hours in the ice bath and 30 minutes at room temperature, the precipitated silver chloride is filtered off with suction and washed with methylene chloride, and the organic phase is washed successively with 20 ml of 1N sodium bicarbonate solution and twice with 15 ml each of water. After drying (MgSO$_4$), the residue of the organic phase is chromatographed on silica gel, deactivated with 10% of water, using cyclohexane:ethyl acetate (5:1), then 2:1). The product fractions yield 1.09 g of 2 as a viscous oil (70%).

$^1$H-NMR (CDCl$_3$): $\delta$=0.10 (s, 6H), 0.85 (s, 9H), 1.22 (d, J=6 Hz, 3H, CHCH$_3$), 2.35-2.55 (m, 4 cyclobutane-H), 3.12 and 3.15 (in each case 1s, 2×3H, OCH$_3$), 3.47 (dd, 3-H) 4.36 (m, CHCH$_3$), 4.77 (d, 2H), CO$_2$CH$_2$), 5.28-5.45 (m, 2H), =CH$_2$), 5.86-6.03 (m, 1=CH), 5.98 (d, J=2.5 Hz, 4-H).

Step B:

A mixture of 515 mg (1 mmol) of 2 and 664 mg (4 mmol) of triethyl phosphite in 27.5 ml of toluene are heated under reflux for 5 hours. The solvent is removed in vacuo and the residue is chromatographed on silica gel, deactivated with 10% of water, using toluene:ethyl acetate (5:1). The product fractions yield 160 mg (33%) of 3 as a colorless resin.

$^1$H-NMR (CDCl$_3$): $\delta$=0.08 (s, 6H), 0.88 (s, 9H); 1.24 (d, J=6 Hz), 3H, CHCH$_3$), 2.10-2.68 (m, 4 cyclobutane-H) 3.12 and 3.14 (in each case 1s, 2×3H, OCH$_3$), 3.65 (dd, J=5 and 1 Hz, 6-H), 3.9-4.1 (m, 1 cyclobutane-H), 4.22 (m, 1H, CHCH$_3$), 4.62-4.72 (m, 2H, CO$_2$CH$_2$), 5.20-5.43 (m, 2H, =CH$_2$), 5.52 (d, J=1 Hz, 5-H), 5.85-6.00 (m, 1 =CH).

Step C:

230 mg (0.48 mmol) of 3 are dissolved in 6 ml of tetrahydrofuran, 300 mg (5 mmol) of acetic acid, followed by 0.64 ml (0.64 mmol) of a 1N Bu$_4$NF solution in tetrahydrofuran are added and the solution is left at 20° C. for 65 hours. After the addition of 30 ml of diethyl ether, the solution is washed with 10 ml of 1N sodium bicarbonate solution and also 3× with 10 ml each of water, dried with magnesium sulfate and the solvent is removed in vacuo. 4 (120 mg, 68%) is obtained as a colorless resin.

$^1$H-NMR (CDCl$_3$); $\delta$=1.36 (d, J=6 Hz, 3H, CHCH$_3$), 2.10-2.70 (m, 4 cyclobutane-H), 3.13 and 3.16 (in each case 1s, 2×3H, OCH$_3$), 3.61 (dd, J=5 and 1 Hz, 6-H), 3.9-4.1 (m, 1 cyclobutane-H), 4.22 (m, 1H, CHCH$_3$) 4.60-4.81 (m, 2H, CO$_2$CH$_2$), 5.22-5.44 (m, 2H, =CH$_2$), 5.58 (d, J=1 Hz, 5-H), 5.87-6.02 (m, 1 =CH).

Step D: Preparation of the title compound 110 mg (0.3 mmol) of 4 are dissolved in a mixture of 1 ml of methylene chloride and 0.4 ml of ethyl acetate under argon. A solution of 60 mg (0.36 mmol) of sodium 2-ethylhexanoate in 0.6 ml of ethyl acetate is then added, followed by 24 mg (0.09 mmol) of triphenylphosphine and 15 mg (0.013 mmol) of tetrakis(triphenylphosphine)-palladium (0). The mixture is stirred at room temperature for 4 hours. 6 ml of water are then added. The aqueous phase is washed 5 times with 10 ml each of methylene chloride and freeze-dried. The residue is chromatographed on XAD-2 using water:isopropanol (10:1). 68 mg (65%) of sodium salt in the form of a yellowish amorphous solid are obtained.

$^1$H-NMR (DMSO-D$_6$); δ=1.13 (d, J=6 Hz), CHCH$_3$), 1.85–2.40 (m, 4 cyclobutane-H), 3.03 and 3.06 (in each case 1s, 2×3H, OCH$_3$), 3.45 (dd, J=5 and 1 Hz, 6-H), 3.90 (m, 1H, CHCH$_3$), 4.40–4.55 (m, 1 cyclobutane-H), 5.40 (d, J=1 Hz), 5-H).

EXAMPLE 4

(5R, 6S)-6-[(1R)-hydroxyethyl]-2-(3-3-ethylenedioxycyclobutyl)-penem-3-carboxylic acid sodium salt

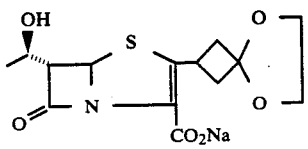

The compound is prepared in analogy to Example 3 by the reaction sequence A→B→C→D from the compound 1 there using 3-3-ethylenedioxycyclobutyl-carbonyl chloride. After chromatography on XAD-2, the sodium salt is obtained as an amorphous colorless solid.

$^1$H-NMR (DMSO-d$_6$): δ=1.14 (d, J=6 Hz, CHCH$_3$), 2.1–2.45 (m, 4 cyclobutane-H), 3.42 (dd, J=5 and 1 Hz, 6-H), 3.70–3.95 (m, 5H, CHCH$_3$ and ethylene), 4.55 (m, 1 cyclobutane-H), 5.25 (bs, OH), 5.40 (d, J=1 Hz, 5-H).

EXAMPLE 5

(5R, 6S)-6-[(1R)-hydroxyethyl]-2-(3-methoxyiminocyclobutyl)-penem-3-carboxylic acid sodium salt

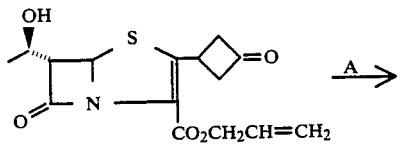

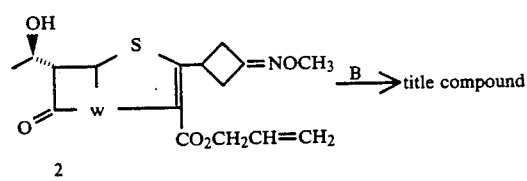

Step A:
194 mg (0.6 mmol) of I are dissolved in 3.6 ml of ethanol and 0.6 ml of methylene chloride and a solution of 1.2 mmol of O-methylhydroxylamine in 2 ml of ethanol are added. After 20 hours at 5° C., the mixture is worked up using ice water and methylene chloride and the residue of the organic phase is chromatographed on a silica gel using toluene:ethyl acetate (2:1). The product fractions give 170 mg of 2 (80%) as a colorless resin.

$^1$H-NMR (CDCl$_3$): δ=1.36 (d, J=6 Hz, CHCH$_3$), 2.88–33.42 (m, 4 cyclobutane-H), 3.72 (dd, J=5 and 1 Hz, 6-H), 3,85 (s, 3H, OCH$_3$), 4.23 (m, 1H, CHCH$_3$), 4.38 (m, 1 cyclobutane-H), 4.62–4.82 (m, 2H, CO$_2$CH$_2$), 5.22–5.45 (m, 2H, =CH$_2$), 5.61 (d, J=1 Hz, 5-H), 5.88–6.04 (m, 1H, =CH).

Step B: Preparation of the title compound
159 mg (0.45 mmol) of 2 are reacted with 82 mg of 2-ethylhexanoic acid potassium salt, 36 mg of triphenylphosphine and 23 mg of tetrakis-(triphenylphosphine)-palladium(0) in analogy to Example 2. The crude product obtained after freeze-drying (104 mg) is purified on XAD-2 (elution using water:isopropanol (10:1). 60 mg (38%) of potassium salt of the title compound are obtained as a colorless amorphous sold.

$^1$H-NMR (D$_2$O): δ=1.31 (d, J=6 Hz, CHCH$_3$), 2.90–3.41 (m, 4 cyclobutane-H), 3.82 (s, 3H, OCH$_3$), 3.88 (dd, J=5 and 1 Hz, 6-H), 4.22 (m, 1H, CHCH$_3$), 4.33–4.48 (m, 1 cyclobutane-H), 5.63 (d, J=1 Hz, 5-H).

EXAMPLE 6

(5R,6S)-6-[(1R)-hydroxyethyl]-2-(3-hydroxyiminocyclobutyl)penem-3-carboxylic acid potassium salt

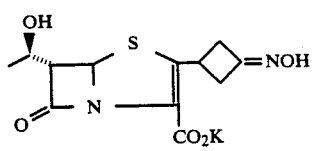

The compound is prepared in analogy to Example 5 from the compound 1 there by reacting with hydroxylamine in ethanol and subsequent removal of the allyl protective group. After chromatography on XAD-2, the potassium salt is obtained as a colorless amorphous solid.

$^1$H-NMR (DMSO-d$_6$): δ=1.16 (d, J=6 Hz, CHCH$_3$), 2.6–3.2 (m, 4 cyclobutane-H), 3.60 (dd, J=5 and 1 Hz, 6-H), 3.86–4.0 (m, 1H, CHCH$_3$), 4.5–4.7 (m, 1 cyclobutane-H), 5.53 (d, J=1 Hz, 5-H).

EXAMPLE 7

Pivaloyloxymethyl (5R,6S)-6-[(1R)-hydroxyethyl]-2-(3-oxocyclobutyl)-penem-3-carboxylate 160 mg (0.5 mmol) of potassium salt of the compound of Example 2 are dissolved in 1.5 ml of dimethyl sulfoxide and 121 mg (0.5 mmol) of pivaloyloxymethyl iodide are added. The mixture is allowed to stand at room temperature for 1 hour. 10 ml of 2% sodium bicarbonate solution are then added to the solution and the mixture is extracted 5×using 5 ml of ethyl acetate each time. The organic phase is washed twice with 5 ml of water each time and dried over MgSO$_4$. The residue of the organic phase is chromatographed on a silica gel, deactivated with 10% water, using toluene:ethyl acetate (2:1). The product fractions give 149 mg (75%) of a yellowish solid.

$^1$H-NMR (CDCl$_3$): δ=1.22 (s, 9H), 1.35 (d, J=6 Hz, CHCH$_3$), 3.15–3.58 (m, 4 cyclobutane-H), 3.72 (dd, J=5 and 1 Hz, 6-H), 4.25 (m, 1H, CHCH$_3$), 4.42 (m, 1 cyclobutane-H), 5.62 (d, J=1 Hz, 5-H), 5.81 and 5.92 (AB, J=6 Hz), CO$_2$CH$_2$).

EXAMPLE 8

1-(Pivaloyloxy)ethyl (5R,6S)-6-[(1R)-hydroxyethyl]-2-(3-oxocyclobutyl)-penem-3-carboxylate The compound is prepared from the potassium salt of Example 2 and (1-pivaloyloxy)ethyl iodide in analogy to Example 7. After chromatographic purification, a 1:1-isomer mixture is obtained as amorphous yellow solid in 20% yield.

$^1$H-NMR (CDCl$_3$): δ=1.18; 120 (each 1s, 9H), 1.38 (2×d, 3H, J=6 Hz, CHCH$_3$), 1.57 (2×d, 3H, CO$_2$CHCH$_3$), 3.12-3.55 (m, 4 cyclobutane-H), 3.72 (2×dd, J=5 and 1 Hz, 6-H), 4.22 (m, 1H, CHCH$_3$), 4.43 (m, 1 cyclobutane-H), 5.61 (2×d, J=1 Hz, 5-H), 6.92 (m, 1 Hz, 1H CO$_2$CHCH$_3$).

EXAMPLE 9

Pivaloyloxymethyl (5R,6S)-6-[(1R)-hydroxyethyl]-2-(3-hydroxyiminocyclobutyl)-penem-3-carboxylate The compound is prepared from the potassium salt of Example 6 and pivaloyloxymethyl iodide in analogy to Example 7. After chromatographic purification, an amorphous yellow solid is obtained.

$^1$H-NMR (CDCl$_3$): δ=1.22 (s, 9H), 1.36 (α, =6 Hz, 3H, CHCH$_3$), 2.92-3.45 (m, 4 cyclobutane-H), 3.72 (dd, J=5 and 1 Hz, 6-H), 4.22 (m, 1H, CHCH$_3$), 4.32 (m, 1 cyclobutane-H), 5.61 (d, J=1 Hz, 5-H), 5.81 and 5.90 (AB, J=6 Hz, CO$_2$CH$_2$).

EXAMPLE 10

(5R,6S)-6-[(1R)-hydroxyethyl]-2-(3-phenyliminocyclobutyl)-penem-3-carboxylic acid tetrabutylammonium salt

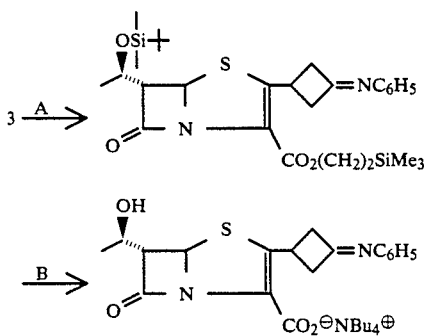

Step A:

A solution of 294 mg (0.5 mmol) of 3 (Example 1), 51 mg (0.55 mmol) of aniline and 5 mg of p-toluene sulfonic acid in 3 ml of toluene is heated under reflux for 1 hour. The solution is chromatographed on a silica gel, deactivated with 10% water, using toluene:ethyl acetate (20:1). After concentrating the product fractions, 250 mg (87%) of a brownish, amorphous solid are obtained.

$^1$H-NMR (CDCl$_3$): δ=0.06 (s, 9H), 0.09 (s, 6H), 0.90 (s, 9H), 1.05 (m, 2H, CH$_2$Si), 1.28 (d, J=6 Hz, 3H, CHCH$_3$), 2.1-2.6 (m, 4 cyclobutane-H), 3.62 (dd, J=5 and 1 Hz, 6H), 4.0-4.3 (m, 4H, 1 cyclobutane-H, CO$_2$CH$_2$ and CHCH$_3$), 5.58 (d, J=1 Hz, 5-H), 6.45, 6.70, 7.05 (each 1, 2 and 2H, arom. H).

Step B:

1.25 ml (1.25 mmol) of a 1N Bu$_4$NF solution in tetrahydrofuran are added to a solution of 1.43 mg (0.25 mmol) of the compound from Step A in 2.5 ml of tetrahydrofuran. After 10 minutes at room temperature, 0.75 ml of 2N acetic acid are added, and the solution is concentrated in vacuo. The resinous residue is digested with 5 ml of ice water, the aqueous solution is discarded, and the resin is dissolved in 2 ml of water:isopropanol(4:1). This solution is chromatographed on XAD-2 adsorbent resin (2×25 cm column) using water-:isopropanol (4:1). The fractions 5-8 (10 ml each) give 40 mg of the title compound as a colorless, amorphous solid after freeze-drying.

$^1$H-NMR (D$_2$O): δ=0.92 (m, 12H, NBu$_4$), 1.33 (m, 11H, 8H, NBu$_4$; 3H, CHCH$_3$), 1.62 (m, 8H, NBu$_4$), 2.2-2.7 (m, 4 cyclobutane-H), 3.18 (m, 8H, NBu$_4$), 3.82 (dd, J=5 and 1 Hz, 6-H), 3.95 (m, 1H, CHCH$_3$), 4.22 (m, 1 cyclobutane-H), 5.60 (d, J=1 Hz, 5H); 6.58, 6.80, 7.12 (each 1, 2 and 2H, arom. H).

We claim:

1. A penem derivative of the formula I

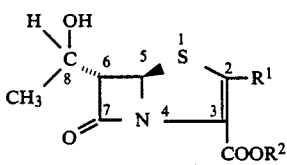

or a pharmaceutically tolerable salt thereof, in which
R$^1$ denotes
C$_3$-C$_6$-oxocycloalkyl
C$_3$-C$_6$-(1,1-bis-C$_1$-C$_3$-alkoxy) cycloalkyl
C$_3$-C$_6$-(1,1-C$_2$-C$_3$-alkylenedioxy) cycloalkyl
C$_3$-C$_6$-(C$_1$-C$_3$-alkylimino) cycloalkyl
C$_3$-C$_6$-aryliminocycloalkyl (where aryl is equal to phenyl, thienyl or furyl)
C$_3$-C$_6$-hydroxyiminocycloalkyl
C$_3$-C$_6$-(C$_1$-C$_3$-alkyloxyimino) cycloalkyl
in which the cycloalkyl radical is unsubstituted, or monosubstituted or disubstituted by C$_1$-C$_3$-alkyl, C$_1$-C$_3$-alkoxy, halogen or methylene
R$^2$ denotes hydrogen
C$_1$-C$_5$-alkanoyloxy-C$_1$-C$_3$-alkyl,
C$_1$-C$_5$-alkoxycarbonyloxy-C$_1$-C$_3$-alkyl,
5-methyl-1,3-dioxolene-2-on-4-yl-methyl phthalidyl
and in which the preferred stereochemistry in position 5 is R, in position 6 is S and in position 8 is R.

2. A compound of the formula I as claimed in claim 1, in which the following substituents and indices have the following meaning:
R$^1$ acetals

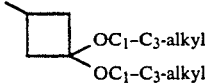

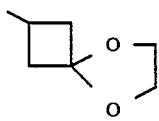 or 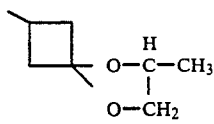

Schiff bases

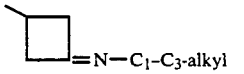 or 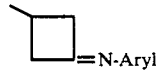

oximes

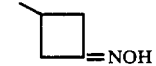 or 

in which n=0–3, and aryl denotes phenyl, thienyl or furyl,

R² hydrogen acetoxymethyl, propionyloxymethyl, isopropionyloxymethyl, N-butyryloxymethyl, isobutyryloxymethyl, pivaloyloxymethyl, isovaleryloxymethyl, 1-acetoxyethyl, 1-acetoxypropyl, 1-pivaloyloxyethyl, 1-methoxycarbonyloxyethyl, 1-ethoxycarbonyloxyethyl, 1-isopropoxycarbonyloxyethyl, methoxycarbonyloxymethyl; phthalidyl,5-methyl-1,3-dioxolen-2-on-4-yl-methyl.

3. A pharmaceutical composition active against bacterial infections which comprises a penem derivative of the formula I as defined in claim 1 or a pharmaceutically tolerable salt thereof together with a pharmacologically tolerable excipient.

4. A method for the treatment of bacterial infections which comprises administering an effective amount of a pharmaceutical composition as claimed in claim 3.

5. A method for the treatment of bacterial infections which comprises administering an effective amount of a compound of the formula I as claimed in claim 1 or a pharmaceutically tolerable salt thereof.

* * * * *